(12) United States Patent
Feriani et al.

(10) Patent No.: US 9,010,657 B2
(45) Date of Patent: Apr. 21, 2015

(54) VOLATILE LIQUID DROPLET DISPENSER DEVICE

(75) Inventors: Amir Feriani, Auvernier (CH); Joseph Hess, Bevaix (CH)

(73) Assignee: Aptar France SAS, Le Neubourg (FR)

( * ) Notice: Subject to any disclaimer, the term of this patent is extended or adjusted under 35 U.S.C. 154(b) by 0 days.

(21) Appl. No.: 12/477,646

(22) Filed: Jun. 3, 2009

(65) Prior Publication Data

US 2009/0314853 A1    Dec. 24, 2009

(30) Foreign Application Priority Data

Jun. 3, 2008  (EP) .................................... 08157455

(51) Int. Cl.
  *B05B 1/08*    (2006.01)
  *A61M 15/00*   (2006.01)
  *B05B 17/00*   (2006.01)
  *B05B 17/06*   (2006.01)

(52) U.S. Cl.
  CPC ........ *A61M 15/0085* (2013.01); *B05B 17/0638* (2013.01); *A61M 2205/0244* (2013.01); *B05B 17/0623* (2013.01)

(58) Field of Classification Search
  CPC .. B05B 17/0638; B05B 17/06; B05B 17/063; B05B 17/0623; B05B 17/0615; B05B 17/0646; B05B 17/0607; A61M 15/0085; A61M 2205/0244
  USPC ................................ 239/102.1, 102.2, 4, 555
  See application file for complete search history.

(56) References Cited

U.S. PATENT DOCUMENTS

| 3,900,162 A | * | 8/1975 | Titus et al. ................. 239/102.2 |
| 4,667,877 A | * | 5/1987 | Yao et al. ................... 239/102.2 |
| 4,667,977 A | | 5/1987 | Lacroix |
| 4,702,418 A | | 10/1987 | Carter et al. |

(Continued)

FOREIGN PATENT DOCUMENTS

| EP | 0 516 565 A1 | 2/1992 |
| EP | 0 516 565 A1 | 12/1992 |

(Continued)

OTHER PUBLICATIONS

International Search Report issued in corresponding European Application No. 07 00 2190, completed Apr. 3, 2007.

(Continued)

*Primary Examiner* — Jason Boeckmann
(74) *Attorney, Agent, or Firm* — Griffin & Szipl, P.C.

(57) ABSTRACT

Volatile liquid droplet dispenser device, comprising: a first substrate having a space for containing liquid, and liquid outlet means for ejecting liquid from the device, the space arranged proximate to the liquid outlet means so liquid may exit the space by traversing the liquid outlet means, a second substrate comprising a support for receiving and holding the first substrate, and a vibrating element arranged to actuate liquid in the space so liquid undergoes vibration and contacts the liquid outlet means thereby exiting the device as a liquid droplet spray, wherein the liquid outlet means comprises a perforated nozzle membrane having a plurality of outlet nozzles, and an actuating element arranged between the vibrating element and the first substrate, and a sealing element arranged between the actuating element and the first substrate, wherein the actuating element and the sealing element are arranged to transmit ultrasound energy to liquid in the space.

23 Claims, 5 Drawing Sheets

(56) References Cited

U.S. PATENT DOCUMENTS

| | | | |
|---|---|---|---|
| 4,923,448 | A | 5/1990 | Ennis, III |
| 5,792,941 | A | 8/1998 | Rye et al. |
| 6,341,732 | B1 | 1/2002 | Martin et al. |
| 6,378,780 | B1 | 4/2002 | Martens et al. |
| 6,439,474 | B2 | 8/2002 | Denen |
| 6,443,366 | B1 | 9/2002 | Hirota et al. |
| 6,536,682 | B1 | 3/2003 | Schnupp et al. |
| 6,554,201 | B2 | 4/2003 | Klimowicz et al. |
| 6,722,582 | B2 | 4/2004 | Hess et al. |
| 6,732,944 | B2 | 5/2004 | Litherland et al. |
| 6,766,817 | B2 | 7/2004 | da Silva |
| 6,802,460 | B2 | 10/2004 | Hess et al. |
| 6,918,404 | B2 | 7/2005 | da Silva |
| 6,926,208 | B2 | 8/2005 | Ivri |
| 7,066,398 | B2 | 6/2006 | Borland et al. |
| 7,066,586 | B2 | 6/2006 | da Silva |
| 7,244,398 | B2 | 7/2007 | Kotary et al. |
| 7,285,255 | B2 | 10/2007 | Kadlec et al. |
| 2002/0162551 | A1 | 11/2002 | Litherland |
| 2002/0162898 | A1 | 11/2002 | Klimowicz et al. |
| 2002/0175220 | A1 | 11/2002 | Pence |
| 2004/0082076 | A1 | 4/2004 | Zengerle et al. |
| 2004/0263567 | A1 | 12/2004 | Hess et al. |
| 2005/0001050 | A1 | 1/2005 | Takagi et al. |
| 2005/0201870 | A1 | 9/2005 | Koerner et al. |
| 2005/0207917 | A1 | 9/2005 | Koerner et al. |
| 2008/0015531 | A1 | 1/2008 | Hird et al. |

FOREIGN PATENT DOCUMENTS

| | | | |
|---|---|---|---|
| EP | 0923957 | A1 | 6/1999 |
| EP | 1 092 541 | A2 | 4/2001 |
| EP | 1 129 741 | A1 | 9/2001 |
| EP | 1129741 | A2 | 9/2001 |
| EP | 1 273 355 | A1 | 1/2003 |
| EP | 1273355 | A1 | 1/2003 |
| EP | 1 604 701 | A1 | 12/2005 |
| EP | 1602414 | A2 | 12/2005 |
| EP | 1604701 | A1 | 12/2005 |
| EP | 1 952 896 | A1 | 8/2008 |
| WO | 95/15822 | A1 | 6/1995 |
| WO | 03068413 | A1 | 8/2003 |
| WO | 2004031580 | A1 | 4/2004 |
| WO | 2005024967 | A1 | 3/2005 |
| WO | 2005097349 | A1 | 10/2005 |
| WO | 2007/062698 | A1 | 6/2007 |
| WO | 2007062698 | A1 | 6/2007 |

OTHER PUBLICATIONS

Hans C. Ohanian, PHYSICS, 452-461, W.W. Norton & Co. 1985.
International Search Report, issued in corresponding application No. EP 08157455.0, completed Oct. 7, 2008, mailed Oct. 14, 2008.
E-mail from Elson da Silva discussing "Know-How and IP in Applied Hydrology," sent Sep. 11, 2008.
European Search Report, completed Apr. 3, 2007, Application No. 07002190.
Office Action issued in co-pending U.S. Appl. No. 12/024,310, dated Jun. 28, 2010.
E-Mail from Elson Silva, "Respecting Hydrology Science—US Pat. Application 20110036921", ECOLAB, Inc., dated Feb. 17, 2011, pp. 1-6.
Hans C. Ohanian, PHYSICS 356-359 (W.W. Norton & Co., Inc. 1985), filed in co-pending related U.S. Appl. No. 12/024,310 as Exhibit A2.
Random House Webster's College Dictionary 87, 903 and 1295 (1991), filed in co-pending related U.S. Appl. No. 12/024,310 as Exhibit B2.
Stephen F. Pond, Inkjet Technology and Product Development Strategies 105-108 (Torrey Pines Research 2000), filed in co-pending related U.S. Appl. No. 12/024,310 as Exhibit C2.
"Vibration Induced Drop Atomization (VIDA)" at http://www.me.gatech.edu/bvukasinovic/VIDA.html, downloaded Aug. 1, 2011 (one page), filed in co-pending related U.S. Appl. No. 12/024,310 as Exhibit D2.
"VIDA Dynamics" at http://me.gatech.edu/bvukasinovic/VIDAdynamics.html, downloaded Aug. 1, 2011 (2 pages), filed in co-pending related U.S. Appl. No. 12/024,310 as Exhibit E2.
Random House Webster's College Dictionary 130 (1991).
Random House Webster's College Dictionary 131, (1991) filed with Amendment G After Final on Sep. 13, 2012 as Exhibit C3.
Office Action issued in co-pending related U.S. Appl. No. 12/095,695 on Apr. 9, 2014.
Office Action issued in co-pending related U.S. Appl. No. 12/024,310 on Mar. 14, 2014.
Office Action issued in co-pending related U.S. Appl. No. 12/095,695 on Oct. 10, 2013.
Random House Webster's College Dictionary 845 (1991).
McGraw-Hill Dictionary of Scientific and Technical Terms 663 (1978).
Hans C. Ohanian, PHYSICS, 390-395 (1985).
Office Action issued in co-pending related U.S. Appl. No. 12/095,695 on Jan. 26, 2015.

* cited by examiner

VOLATILE LIQUID DROPLET DISPENSER DEVICE

This application claims priority from European Patent Application No. 08 157 455.0, filed Jun. 3, 2008, the entire disclosure of which is incorporated herein by reference.

FIELD OF THE INVENTION

The present invention relates to a droplet dispensing device.

BACKGROUND OF THE INVENTION

Such droplet dispensing devices are also sometimes called aerosol generators, nebulizers and the like. They normally contain a nozzle body on a support part, in particular, a nozzle body of a liquid droplet spray device which dispenses a liquid substance as a liquid droplet spray or from the device through the nozzles of the nozzle body. They further consist of an actuator based on a vibrating element which generally causes the liquid to vibrate, to be accelerated and expelled as droplets. They further consist of elements such as liquid space, liquid feed and fluid interface to a reservoir, a reservoir as well as electrical connections between the vibrating element and a corresponding electronic circuitry. The elements may be contained in the aforementioned support part, in a further support part or they may be contained in a number of support parts. The support part or parts and elements need to be manufactured and assembled with the actuator and the vibrating element. The liquid may be for example an ambient fragrance, a perfume, an insecticide, a liquid pharmaceutical formulation, aqueous based liquids and flammable or combustible liquids.

Such nozzle bodies are sometimes called aperture plates, nozzle arrays, dosing aperture, orifice plate, vibratable membrane member, dosing aperture arrangement, aerosol generator and the like. The terms are hence to be understood as being interchangeable throughout the present document.

In fact, such nozzle bodies and droplet spray devices are well known. For example see the document EP 1 129 741 in the name of the present Applicant. This document describes a liquid droplet spray device having a top substrate formed of a main body and of a nozzle body. The nozzle body contains a nozzle array of liquid droplet outlet means allowing a liquid substance contained in the liquid droplet spray device to exit the device, in this case as a spray of droplets. The nozzle body is conventionally formed of a nozzle array made out of silicon, a polymer, a resin such as SU-8, Nickel, a metal alloy, Parylen, Duroplast or any suitable material or combination of these and other materials that allows for a sufficiently precise and cost-effective manufacturing of the outlet nozzle array. Beyond well-known silicon, metal and SU-8 resin micro-machining methods the nozzle array could also be produced by methods using tools made with silicon micro-machining and other known replication methods like LIGA (Lithography-Galvano forming), hot embossing, UV printing, polymer and powder micro-injection moulding, micro-EDM and similar advanced 3D micro-machining methods and suitable combination of methods using photolithography and micro-structuring of resins, silicon, metal and plastic.

The documents U.S. Pat. No. 6,722,582 and EP 1 273 355 also in the name of the present applicant disclose such micro-machining methods.

The document PCT/EP2006/006059, in the name of the present Applicant, shows a droplet spray device including the nozzle body, the support parts and the actuator containing the vibrating element as well as a general way of assembling such a device.

Documents US 2004/0263567 and EP-A-1 604 701 also in the name of the present Applicant, show examples of various device configurations for which such a droplet spray device can be produced and needs to be assembled into in an efficient and cost-effective manner.

Another device is known from the document U.S. Pat. No. 4,702,418 which describes a piezoelectric aerosol dispenser that has eccentric liquid inlet/outlet means, and a nozzle chamber having a nozzle region proximate a single nozzle and a larger reservoir interconnected to the nozzle region. The nozzle region is gravity fed through a restrictive channel. Further, a piezoelectric bender is used to drive fluid from the reservoir region to the nozzle region and from the nozzle region through the single nozzle to create an aerosol spray. Such an arrangement with a piezoelectric bender does not allow for a controlled release of fluid, as the fluid must first be pumped from the reservoir region and then expelled from the nozzles without interference of one flow with the other. Further, precise control while using a piezoelectric bender is virtually impossible.

As can be seen from the cited prior art documents, all of them approach mainly a particular aspect of the manufacturing of a particular component of the respective droplet spray devices, but fail to take a total device approach to the industrial production and assembly of components and device. In fact these devices, together with others fall into the category of Multi-Material-Electro-Mechanical Systems. Generally, the construction, the production and the assembly of such devices requires to dominate several main criteria or problems which additionally to attaining the lowest possible cost may present contradictory effects and conditions.

The effects and conditions firstly refer to the need to provide capillary feed or feed at very low pressures well below one mbar (100 Pa) or fractions thereof. Capillary feed for some liquids will refer to liquid channel, chamber and other fluid handling structures or features with dimensions of a few hundred microns to below 100 μm, often in the range of 10 to 50 μm, absolute evenness and smoothness of wetted surfaces and absence of dead spaces, corners and pockets in order to avoid even minute bubble traps. These bubbles, consisting of air surrounded by an ultra-thin film of the liquid, tend to block the capillary feed, hence the device functionality in a very effective manner.

The second problem is to assemble the actuator in a way which provides the most efficient use of the ultrasonic energy delivered by the vibrating element, namely a piezoelectric element.

The third problem is that leak-tightness needs to be guaranteed for a variety of liquids. Leak-tightness normally implies rigid body construction and assembly of its components and long-term resistance of the components to sometimes aggressive solvents.

A further problem is the aforementioned lowest possible production cost together with a minimum of assembly operations in simple, reliable assembly steps.

A further problem is represented by the need to disassemble the droplet spray device after one or several uses in order not to discard all parts after use, but to discard only one part and to keep the others for further use after cleaning for example or to disassemble some parts for cleaning them periodically and to reassemble them again for further use.

As can be understood by the person skilled in the art, these criteria can be highly contradictory in their requirements and effects. Also, as said before, none of the prior art devices discloses on how to achieve these contradictory criteria in one device or a family of devices.

Other prior art devices have addressed in more detail some individual problem areas. For example, document U.S. Pat. No. 6,926,208 discloses a fluid injection device with an aperture plate having an oscillating surface with tapered apertures thereon and various relatively complex combinations of fluid supply to the oscillating surface. Again this document is in general silent about how this feature can be integrated into a final device providing leak-tightness, fluidic optimization and low cost integration.

In view of the above problems, the present Applicant has filed a co-pending application EP 07 002 190.2 relating to a dispensing device that overcomes the abovementioned problems.

This document EP 07 002 190.2 describes a volatile liquid dispenser device for ejecting liquid as a spray of droplets. A piezoelectric element acts on the liquid so as to cause the liquid to undergo vibration by transmission of the ultrasound from the piezoelectric element to the liquid. This device is schematically shown in FIG. 1, which shows a detailed view of a cross-section cut of the dispensing device, which comprises a first substrate 1 and a second substrate 3. An actuating membrane 2 is positioned between first substrate 1 and second substrate 3, and can be actuated, i.e. put into vibration, by way of a vibrating element 6 suitably attached thereto.

First substrate 1 is provided with a space 5, for example a recessed portion, allowing to receive liquid that is to be expelled through ultrasound transmission from the vibrating element 6 to the liquid. This space 5, once filled with liquid, thus constitutes a pressure chamber for ejecting the liquid contained therein. First substrate 1 further comprises liquid droplet outlet means 4 suitably arranged to allow for ejection of the liquid there through. This liquid droplet outlet means 4 generally is a spray head consisting of a perforated membrane having a nozzle array, in a manner well known in the art.

However, the Applicant has found that this device only partially addresses the above-mentioned problem relating to efficiency of ultrasonic sound transmission so as to allow for improved efficiency of a piezoelectric element for actuating the liquid to be expelled. It seems that some transmission efficiency is lost from vibrating element 6 to actuating element 6 and then to liquid in space 5.

If this ultrasonic sound transmission can be further improved, a reduction in power consumption can be achieved, which is important especially when using battery-powered devices.

Also, this device has a further problem in that space 5 of the first substrate for containing liquid is formed as a recessed opening in the first substrate. This means that the first substrate cannot be dissociated from second substrate 3 when liquid is present in space 5, as the liquid will spill out. This leads to undesirable assembly constraints.

It is, therefore, an object of the present invention to provide an innovative droplet spray device that overcomes the inconveniences presented by the prior art documents.

Thus, the present invention concerns the construction of an innovative dispenser device fulfilling these objectives efficiently and in various embodiments which may be obtained in a relatively simple and inexpensive manner.

SUMMARY OF THE INVENTION

The innovative dispenser device is a volatile liquid droplet dispenser device for ejecting a liquid as a spray of droplets. In accordance with a first embodiment of the present invention, a volatile liquid droplet dispenser device, for ejecting a liquid as a spray of droplets, comprises: (a) a first substrate (1) having a space (5) for containing the liquid, and having liquid outlet means (4) for ejecting liquid from the device, the space (5) being arranged proximate to the liquid outlet means (4) such that the liquid may exit the space (5) of the device by traversing the liquid outlet means (4) (b) a second substrate (3) comprising a support for receiving and holding the first substrate (1), (c) a vibrating element (6) arranged to actuate liquid substance in the space (5) such that the liquid undergoes a vibration and contacts the liquid outlet means (4) thereby exiting the device as a liquid droplet spray, wherein the liquid outlet means (4) of the first substrate comprises a perforated nozzle membrane having a plurality of outlet nozzles, wherein the dispensing device further comprises an actuating element (12, 22) arranged between the vibrating element (6) and the first substrate (1), and a sealing element (7) arranged between the actuating element (12, 22) and the first substrate (1) for sealing the space (5), the actuating element (12, 22) and the sealing element (7) being arranged to transmit ultrasound energy generated by vibration of the vibrating element (6) to liquid in the space (5).

In accordance with a second embodiment of the present invention, the first embodiment is modified so that the actuating element (12, 22) is shaped and structured so as to allow for efficient ultrasound energy transmission from the vibrating element (6) to the sealing element (7). In accordance with a third embodiment of the invention, the second embodiment is further modified so that the actuating element is horn-shaped (12) or step-shaped.

In accordance with a fourth embodiment of the invention, the first, second and/or third embodiments are further modified so that the sealing element (7) has a top surface (7a) forming the bottom surface of the space (5), and the top surface (7a) has one or more stepped portions extending from the surface (7a) into the space (5). In accordance with a fifth embodiment of the present invention, the first, second, third, and/or fourth embodiments are further modified so that they further include an insert (15) arranged in the space (5).

In accordance with a sixth embodiment of the invention, the fifth embodiment is further modified so that the insert (15) is disc-shaped and is sized to substantially correspond to the bottom surface of the space (5). In accordance with a seventh embodiment of the invention, the fifth or sixth embodiment is further modified so that the insert (15) has a top surface (15a) having one or more stepped portions extending from the surface.

In accordance with an eighth embodiment of the present invention, the first, second, third, fourth, fifth, sixth, and/or seventh embodiments of the present invention are further modified so that the first substrate (1), the liquid outlet means (4), the space (5) and the sealing element (7) together form a separable part of the dispenser device. In accordance with a ninth embodiment of the present invention, the eighth embodiment is further modified so that the separable part is disposable. In accordance with a tenth embodiment of the present invention, the eighth or ninth embodiments are further modified so that the space (5) is pre-filled with liquid to be expelled, and the separable part constitutes a disposable liquid cartridge.

In accordance with an eleventh embodiment of the present invention, the first embodiment, the second embodiment, the third embodiment, the fourth embodiment, the fifth embodiment, the sixth embodiment, the seventh embodiment, the eighth embodiment, the ninth embodiment, and/or the tenth embodiment are further modified so that the vibrating element (6) is a piezoelectric vibrator.

Thanks to the construction of the innovative and inventive dispenser device according to the present invention an efficient device fulfilling these objectives in various embodiments may be obtained in a relatively simple and inexpensive manner.

BRIEF DESCRIPTION OF THE DRAWINGS

Other features and advantages of the dispenser device according to the present invention will become clear from reading the following description, which is given solely by way of a non-limitative example thereby referring to the attached drawings in which.

DETAILED DESCRIPTION OF THE INVENTION

Examples of preferred embodiments will now be described. Generally, the volatile liquid droplet dispenser device according to the present invention comprises a first substrate, also called a top packaging, and a second substrate, also called a bottom packaging, mounted one onto the other, and arranged to receive liquid from a liquid reservoir, which may be external or internal. The assembled device is also called an atomiser, as it is arranged to atomise, i.e. to create a liquid droplet spray of the liquid received from the reservoir.

Figure 2:
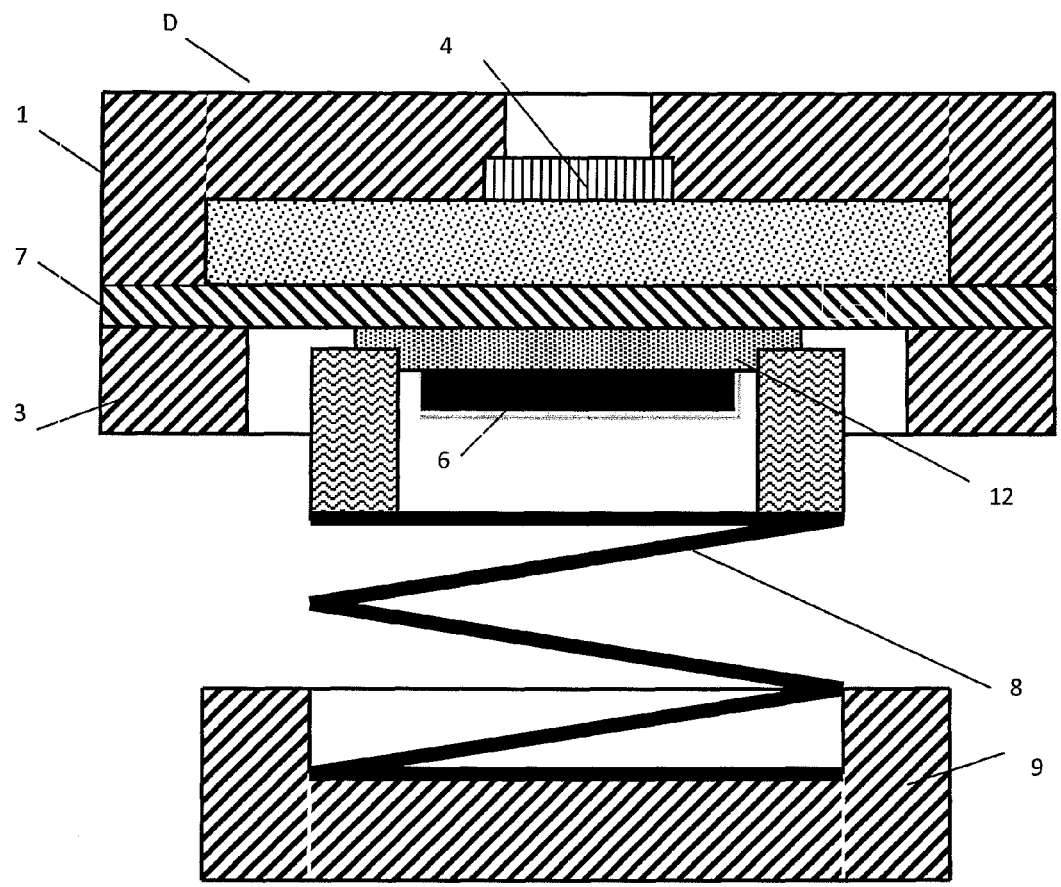
FIG. 2 shows a schematic cross-sectional view of a dispenser device according to the present invention in a first embodiment.

FIG. 2 shows a detailed view of a cross-section cut of a dispensing device according to the present invention in a first embodiment. Dispensing device D comprises a first substrate 1 and a second substrate 3. First substrate 1 has a space 5 for containing liquid to be expelled, and further has liquid outlet means 4 for ejecting liquid from the space and thus from the device. Space 5 is arranged proximate to liquid outlet means 4 such that the liquid may exit the space 5 of the device by traversing liquid outlet means 4. Similar to the conventional device disclosed in the above-mentioned co-pending application EP 07 002 190.2, liquid outlet means 4 may comprise a perforated nozzle membrane having a plurality of outlet nozzles. Second substrate 3 may comprise a support for receiving and holding first substrate 1.

An actuating element or membrane 12 is positioned between first substrate 1 and second substrate 3, and can be actuated, i.e. put into vibration, by way of a vibrating element 6. A further element, sealing membrane 7 is provided between actuating membrane 12 and first substrate 1 and seals space 5.

Vibrating element 6 is fixed to actuating membrane 12, which itself is arranged to be in contact with sealing membrane 7. As such, when vibrating element 6 is activated, the ultrasound energy generated by vibrating element 6 is transmitted to actuating membrane 12, to sealing membrane 7 and then to liquid present in space 5, thus causing the liquid to undergo vibrations and to be expelled as a spray of droplets.

Second substrate 3 is further attached to a support part 9 which may comprise a spring 8 to ensure correct contact between actuating membrane 12 and sealing membrane 7.

In fact, these membranes are arranged in contact relationship, but need not be fixedly attached to each other.

As shown in FIG. 2, the first substrate 1 may be generally identical to that described in abovementioned co-pending application EP 07 002 190.2. Further, second substrate 3 may also be generally identical to that described in abovementioned co-pending application EP 07 002 190.2.

In fact, the main difference between the present dispensing device and that of the co-pending application lies in the use of intermediate sealing membrane 7.

The Applicant has found that, contrary to what night be expected, the ultrasound energy is more efficiently transmitted to liquid in space 5 when using such intermediate sealing membrane 7.

Indeed, in this arrangement, actuating membrane 12 can be optimised to allow for efficient transmission by pairing it with vibrating element 6. First of all, it may be fixedly attached to vibrating element 6. Further, it can be configured sufficiently thick to ensure good contact with vibrating element, and to allow for fully optimised transmission of ultrasound of both elements together. Correct pairing of these elements may be achieved by using impedance-matching technique, as may be readily understood by a skilled person.

Figure 1:
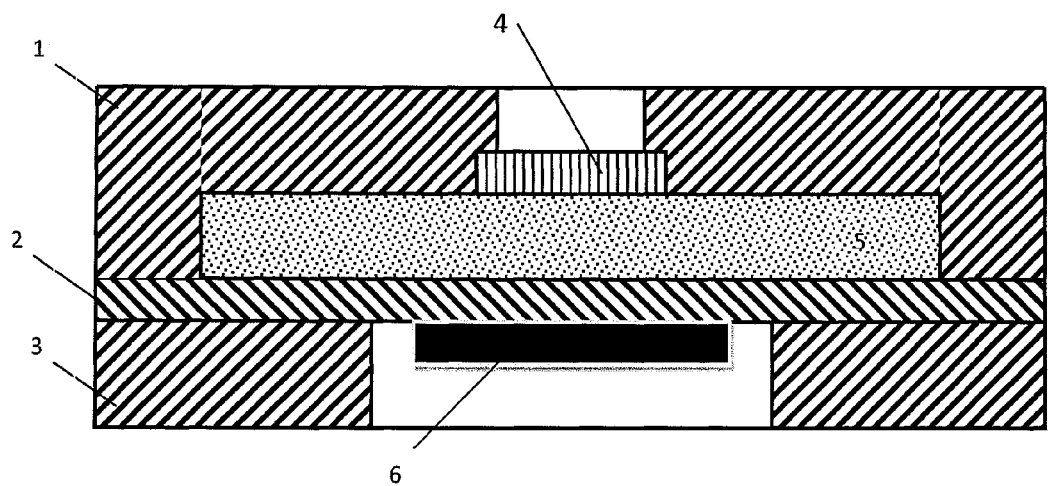
FIG. 1, previously described, shows a schematic cross-sectional view of a conventional volatile liquid dispenser device.

By further using a separate sealing membrane 7, which may be chosen as a very thin membrane, and may be thinner than the actuating membrane 2 of the prior art device shown in FIG. 1, a more efficient transmission of the ultrasound energy is possible from the pair actuating membrane 12/vibrating element 6 to liquid in space 5.

Figure 3:
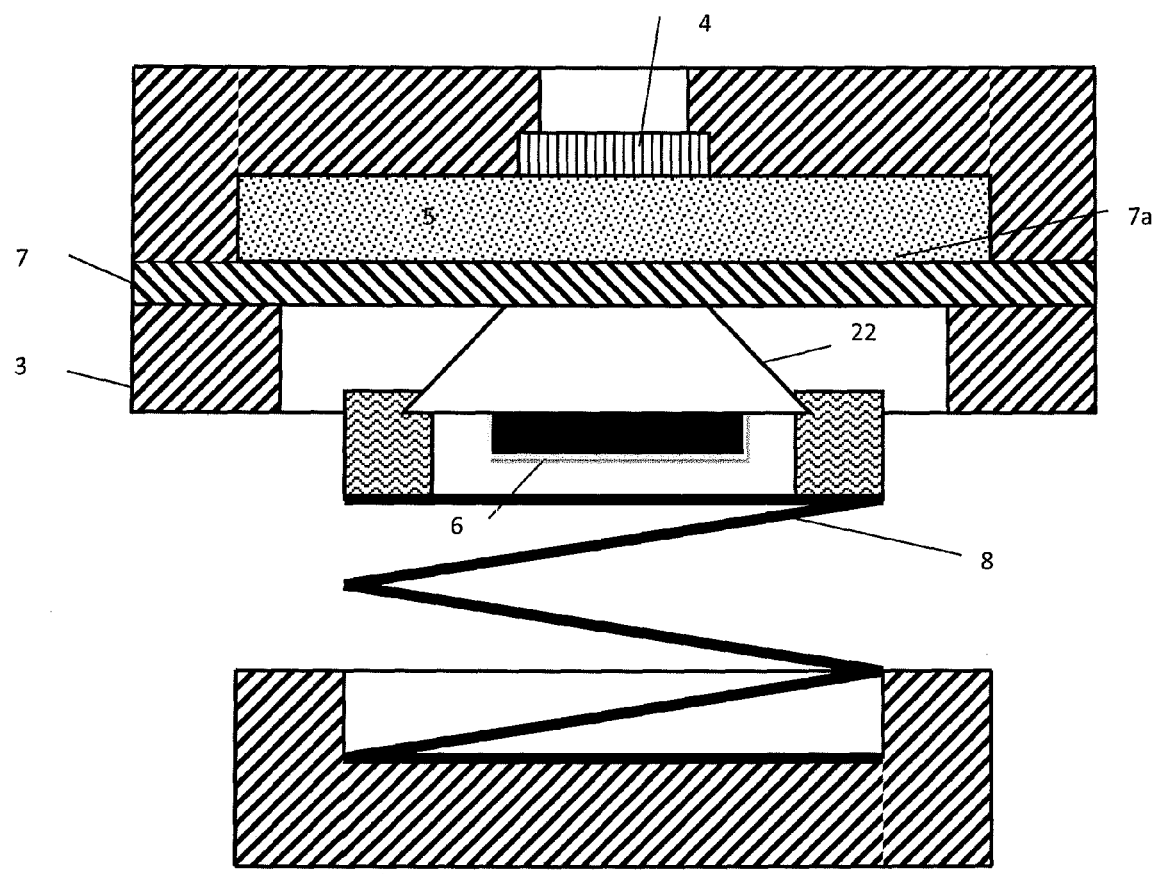
FIG. 3 shows a schematic cross-sectional view of a dispenser device according to the present invention in a second embodiment.

FIG. 3 shows a detailed view of a cross-section cut of a dispensing device according to the present invention in a second embodiment. Like elements as shown in FIG. 2 are identified by the same reference numeral, so that no further description thereof is provided here.

The only difference in this second embodiment as compared to the above-described first embodiment relates to actuating element 22, which here has a horn-shape, tapering towards sealing membrane 7. Actuating membrane 22 is fixedly attached to vibrating element, and this pair is arranged so as to be aligned with the outlet means 4 of the dispensing device so as to allow for optimal use of the generated ultrasound energy.

Thus, as can be seen, the main difference between the first embodiment and the second embodiment lies in the shape of the actuating element.

In fact, again it was found that by using an additional membrane, i.e. sealing membrane 7 in between actuating membrane 22 and first substrate 1, it becomes possible to allow for an optimal design of the pair consisting of the actuating membrane 22 and vibrating element 6, as far as ultrasound energy transmission is concerned.

In general, Applicant has thus found that by designing the actuating membrane in such a manner that it is structured to optimize ultrasound transmission, a more efficient dispenser device can be obtained, which thus uses less power.

Such structuring of the actuating membrane may be as shown above in FIGS. 2 (generally flat-shaped) and 3 (generally horn-shaped), but it may of course also have a different shape, such as step-shaped, allowing to efficiently transmit the ultrasound energy by a correct pairing with the vibrating element.

Further, thanks to the use of intermediate sealing member 7, and by fixedly attaching the latter to first substrate 1, thus enclosing and sealing space 5, it is possible to obtain a separable part consisting of first substrate 1, sealing membrane 7, and outlet means 4. In fact, such separable part is self-contained and may include pre-filled liquid in space 5, or not, as any liquid will not seep out due to the presence of sealing membrane 7.

Advantageously, this self-contained part may be designed to be disposable, thus allowing for simple replacement of liquid, and avoiding any clogging of the nozzles in the perforated membrane over time. The second substrate, the actuating membrane and the vibrating element may on the contrary be designed as non-disposable parts.

In a variant, an external reservoir, not shown, may be provided for feeding liquid from the reservoir to space 5, in a manner known as such, and also described for example in co-pending application EP 07 002 190.2. Suitable capillary liquid feeding means, not shown, are then required for transmitting the liquid from the external reservoir to space 5, in a manner well known to a skilled person. Space 5 may be designed to receive a predetermined quantity of liquid, such as a unit dose. Space 5 may instead, however, be designed sufficiently large to act as an internal reservoir thus avoiding the need of an external reservoir.

In such manner, a separate disposable cartridge can be obtained which may be fitted onto second substrate 3, thereby ensuring contact between sealing membrane 7 and actuating element 12 or 22.

In a further improvement of the present dispensing device, the Applicant has found that the ultrasound energy transmission may be further optimised by adaptation of the inner space of space 5.

Figure 4:
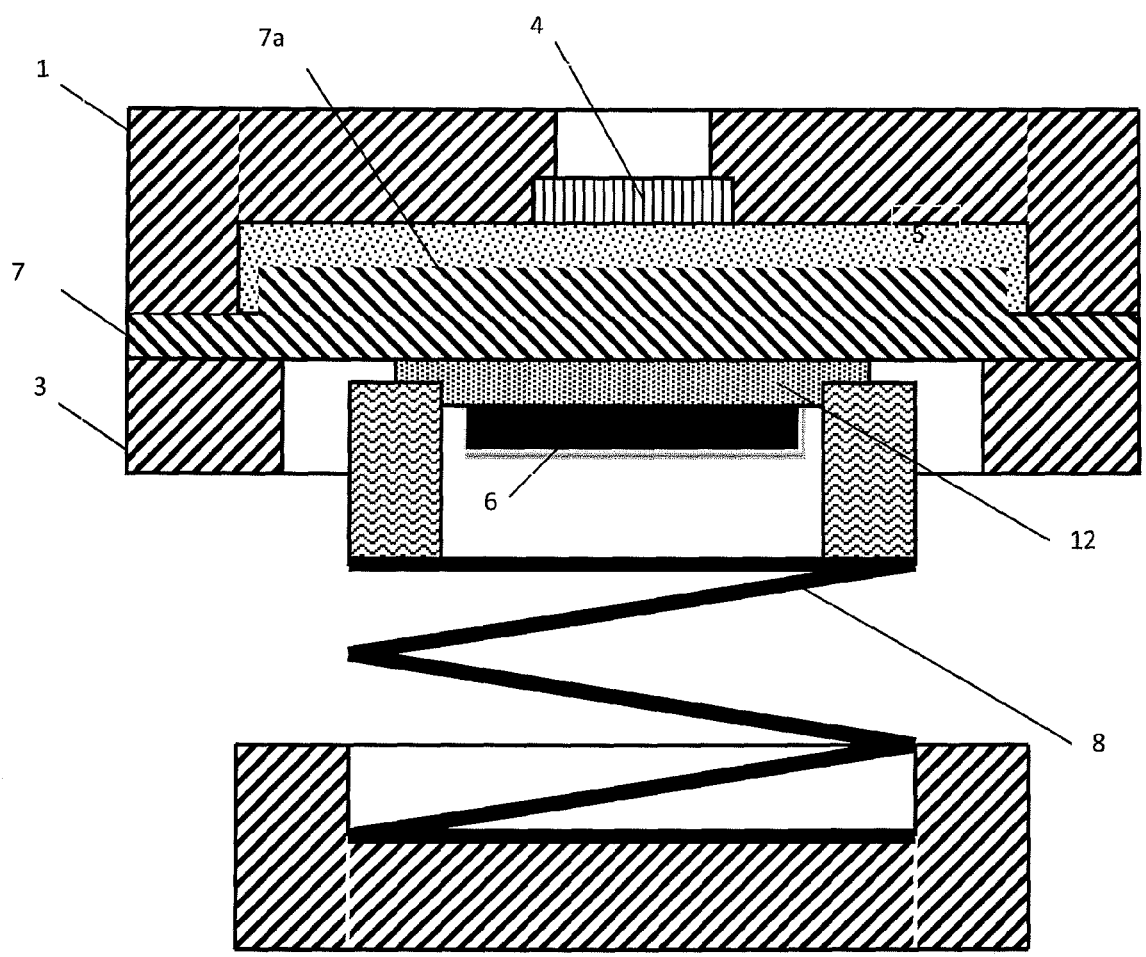
FIG. 4 shows an improvement of the dispenser device according to the present invention.

In fact, as shown in FIG. 4, by providing a structured top surface 7a of sealing membrane 7, such structured top-surface 7a thus constituting the bottom of space 5, a further improved ultrasound energy transmission is obtained. In fact, as shown in the figure, one or more bumps or steps may be provided on this top surface 7a to this effect.

Such structuring causes a slightly more compact space height thus improving capillarity within space 5, and allowing liquid to more easily reach outlet means 4.

Figure 5:
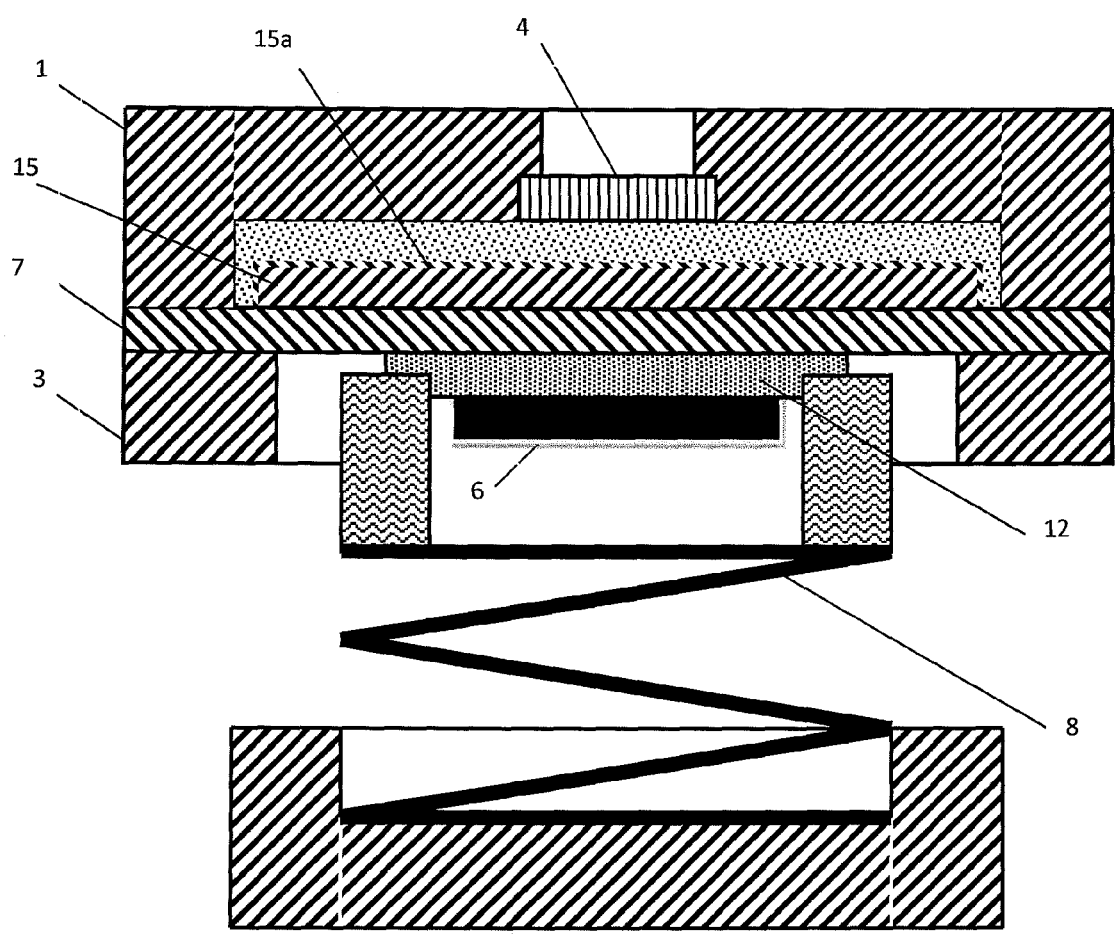
FIG. 5 shows a further improvement of the dispenser device according to the present invention where an insert is provided in the space for containing liquid to be expelled.

Further, instead of using a structured top surface, or even in combination with such structured top surface 7a, an insert 15 may be provided in space 5, as shown in FIG. 5.

Such insert 15 may be a soft porous medium for absorbing the liquid present in space 5. It may also be a thin foil, or a disk-shaped element. Again, such insert allows for improved capillarity within space 5. Insert 15 may itself have a top structured surface 15a, similar to top surface 7a of sealing membrane 7.

Figure 6:
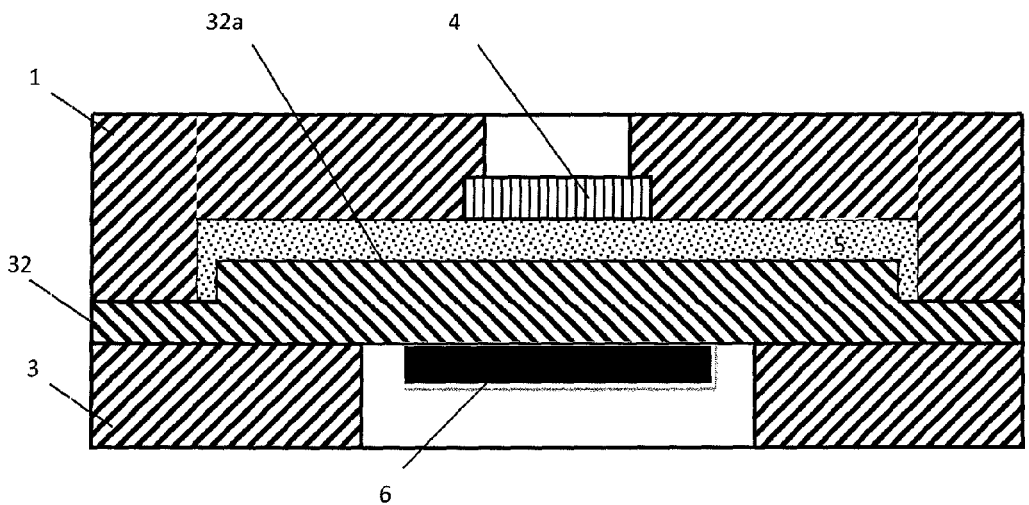
FIG. 6 shows an alternative arrangement of the dispenser device according to the present invention.

In an alternative arrangement, and as shown in FIG. 6, top surface 32a of actuating membrane 32 may be structured to improve capillarity, in the same manner as explained above for top surface 7a of the sealing membrane 7. In this alternative arrangement, no sealing membrane is used. Instead, actuating membrane 32 is fixed directly to first substrate 1, similar to the prior art arrangement shown in FIG. 1. Further, this actuating membrane 32 may be shaped and structured in the same manner as actuating membranes 12 or 22 of FIGS. 2 and 3, i.e. this actuating membrane 32 may also have a horn-shape, or a step-shape, or have another suitable form in order to optimize ultrasound energy transmission from vibrating element 6 to liquid in space 5, in a similar manner as already explained above with respect to the embodiments shown in FIGS. 2 and 3.

Figure 7:
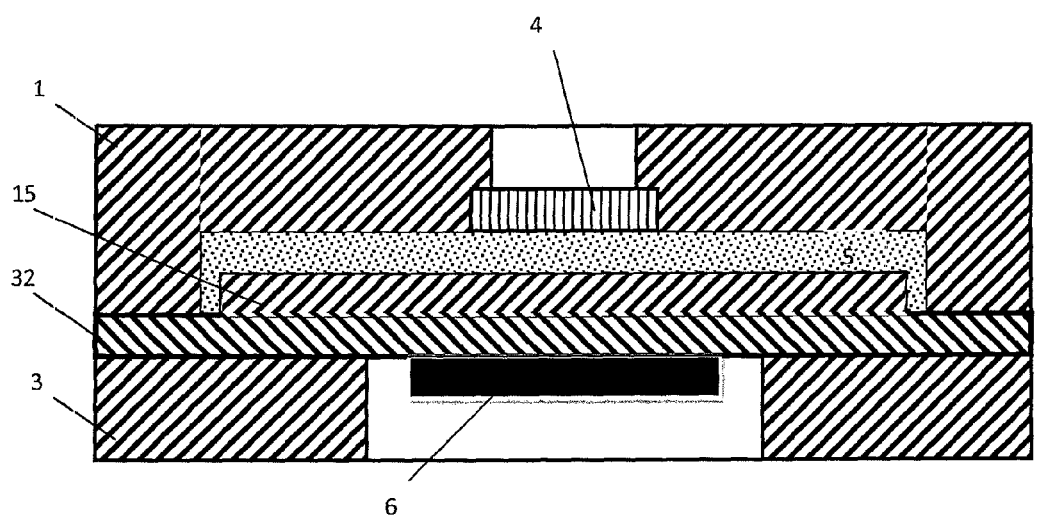
FIG. 7 shows a variant of the alternative arrangement shown in FIG. 6 of the dispenser device according to the present invention.

As further shown in FIG. 7, in the alternative arrangement of FIG. 6, an insert 15 may also be used, instead of structuring top surface 32a of actuating membrane 32. Such insert may be identical to that as shown in FIG. 5, and thus allows improving capillarity by slightly reducing the volume of space 5.

Thanks to the above-described embodiments of the dispensing device according to the present invention, ultrasound energy transmission can be improved, thus leading to improved fluidic performance of the dispensing device. As capillarity characteristics may further be optimised too, a further increase in fluidic performance may be obtained. As may be understood, this leads to a more efficient device, requiring less ultrasound transmission for ejecting a similar amount of liquid as compared to the conventional device as disclosed by co-pending application EP 07 002 190.2, so that less energy is required to operate the device, which is of course an important aspect, not only in a battery-powered liquid droplet dispensing device, but in general.

Having described now the preferred embodiments of this invention, it will be apparent to one of skill in the art that other embodiments incorporating its concept may be used. It is felt, therefore, that this invention should not be limited to the disclosed embodiments, but rather should be limited only by the scope of the appended claims.

The invention claimed is:

1. A volatile liquid droplet dispenser device for ejecting a liquid as a spray of droplets, the device comprising:
   (a) a first substrate having a space for containing liquid, and having liquid outlet means for ejecting liquid from the device, wherein the space is arranged proximate to the liquid outlet means so that liquid may exit the space of the device by traversing the liquid outlet means;
   (b) a second substrate comprising a support for receiving and holding the first substrate;
   (c) a vibrating element arranged to actuate liquid in the space so that liquid undergoes a vibration and contacts the liquid outlet means so that liquid exits the device as a liquid droplet spray, wherein the liquid outlet means of the first substrate comprises a perforated nozzle membrane having a plurality of outlet nozzles;
   (d) an actuating element arranged between the vibrating element and the first substrate; and
   (e) a sealing membrane arranged, between the actuating element and the first substrate and between the second substrate and the first substrate such that a substantial part of the sealing membrane is in direct contact with the actuating element, the sealing membrane being arranged to entirely seal one end of the space, wherein the sealing membrane is sandwiched between the first substrate and the second substrate so as to contact both the first substrate and the second substrate, wherein ultrasound energy is generated by vibration of the vibrating element and the ultrasound energy is transmitted from the vibrating element through the actuating element and thence through the substantial part of the sealing membrane to directly actuate liquid in the space.

2. A volatile liquid droplet dispenser device according to claim 1, wherein said actuating element is shaped and structured so as to allow for efficient ultrasound energy transmission from said vibrating element to said sealing membrane.

3. A volatile liquid droplet dispenser device according to claim 1, wherein said sealing membrane has a top surface forming a bottom surface of said space, and said top surface has one or more stepped portions extending from said top surface into said space.

4. A volatile liquid droplet dispenser device according to claim 1, further comprising an insert arranged in said space.

5. A volatile liquid droplet dispenser device according to claim 4, wherein said insert is disc-shaped and is sized to substantially correspond to the bottom surface of said space.

6. A volatile liquid droplet dispenser device according to claim 4, wherein said insert has a top surface having one or more stepped portions extending from the surface.

7. A volatile liquid droplet dispenser device according to claim 1, wherein said first substrate, said liquid outlet means, said space and said sealing membrane together form a separable part of said dispenser device.

8. A volatile liquid droplet dispenser device according to claim 7, wherein said separable part is disposable.

9. A volatile liquid droplet dispenser device according to claim 7, wherein said space is pre-filled with liquid to be expelled, and said separable part constitutes a disposable liquid cartridge.

10. A volatile liquid droplet dispenser device according to claim 1, wherein said vibrating element is a piezoelectric vibrator.

11. A volatile liquid droplet dispenser device according to claim 2, wherein said sealing membrane has a top surface forming a bottom surface of said space, and said top surface has one or more stepped portions extending from said top surface into said space.

12. A volatile liquid droplet dispenser device according to claim 2, further comprising an insert arranged in said space.

13. A volatile liquid droplet dispenser device according to claim 3, further comprising an insert arranged in said space.

14. A volatile liquid droplet dispenser device according to claim 11, further comprising an insert arranged in said space.

15. A volatile liquid droplet dispenser device according to claim 2, wherein said actuating element is step-shaped.

16. A volatile liquid droplet dispenser device for ejecting a liquid as a spray of droplets, the device comprising:
   (a) a first substrate having a space for containing liquid, and having liquid outlet means for ejecting liquid from the device, wherein the space is arranged proximate to the liquid outlet means so that liquid may exit the space of the device by traversing the liquid outlet means;
   (b) a second substrate comprising a support for receiving and holding the first substrate;
   (c) a vibrating element arranged to actuate liquid in the space so that liquid undergoes a vibration and contacts the liquid outlet means so that liquid exits the device as a liquid droplet spray, wherein the liquid outlet means of the first substrate comprises a perforated nozzle membrane having a plurality of outlet nozzles;
   (d) an actuating element arranged between the vibrating element and the first substrate; and
   (e) a sealing element arranged between the actuating element and the first substrate and between the second substrate and the first substrate for sealing the space,
   wherein the actuating element and the sealing element are arranged to transmit ultrasound energy generated by vibration of the vibrating element to liquid in the space, and
   wherein the actuating element is shaped and structured so as to allow for efficient ultrasound energy transmission from the vibrating element to the sealing element, and the actuating element is horn-shaped tapering towards the sealing element.

17. A volatile liquid droplet dispenser device according to claim 16, wherein said sealing element has a top surface forming a bottom surface of said space, and said top surface has one or more stepped portions extending from said top surface into said space.

18. A volatile liquid droplet dispenser device according to claim 16, further comprising an insert arranged in said space.

19. A volatile liquid droplet dispenser device according to claim 17, further comprising an insert arranged in said space.

20. A volatile liquid droplet dispenser device for ejecting a liquid as a spray of droplets, the device comprising:
   (a) a first substrate having a space for containing liquid, and having liquid outlet means for ejecting liquid from the device, wherein the space is arranged proximate to the liquid outlet means so that liquid may exit the space of the device by traversing the liquid outlet means;
   (b) a second substrate comprising a support for receiving and holding the first substrate;
   (c) a vibrating element arranged to actuate liquid in the space so that liquid undergoes a vibration and contacts the liquid outlet means so that liquid exits the device as a liquid droplet spray, wherein the liquid outlet means of the first substrate comprises a perforated nozzle membrane having a plurality of outlet nozzles;
   (d) an actuating element arranged between the vibrating element and the first substrate;
   (e) a sealing element arranged between the actuating element and the first substrate and between the second substrate and the first substrate for sealing the space; and
   (f) a support part that comprises a spring, wherein the spring is disposed to ensure contact between the actuating element and the sealing element, and wherein the actuating element and the sealing element are arranged to transmit ultrasound energy generated by vibration of the vibrating element to liquid in the space.

21. A volatile liquid droplet dispenser device according to claim 1, wherein a top surface of the sealing membrane constitutes a bottom of the space so that the sealing membrane both encloses and seals the space.

22. A volatile liquid droplet dispenser device according to claim 21, wherein the actuating element and the sealing membrane are paired together so that the actuating element contacts a center portion of the sealing membrane.

23. A volatile liquid droplet dispenser device for ejecting a liquid as a spray of droplets, the device comprising:
   (a) a first substrate having a space for containing liquid, and having liquid outlet means for ejecting liquid from the device, wherein the space is arranged proximate to the liquid outlet means so that liquid may exit the space of the device by traversing the liquid outlet means;
   (b) a second substrate comprising a support for receiving and holding the first substrate;
   (c) a vibrating element arranged to actuate liquid in the space so that liquid undergoes a vibration and contacts the liquid outlet means so that liquid exits the device as a liquid droplet spray, wherein the liquid outlet means of the first substrate comprises a perforated nozzle membrane having a plurality of outlet nozzles;
   (d) an actuating element arranged between the vibrating element and the first substrate; and
   (e) a sealing membrane arranged, between the actuating element and the first substrate, between the second substrate and the first substrate, and between the space and the actuating element to seal one end of the space from the actuating element and the vibrating element, wherein the sealing membrane is sandwiched between the first substrate and the second substrate so as to contact both the first substrate and the second substrate, wherein ultrasound energy is generated by vibration of the vibrating element and the ultrasound energy is transmitted from the vibrating element through the actuating element, and then through the sealing membrane, and from the sealing membrane directly to actuate liquid in the space.

* * * * *